United States Patent [19]
Luther et al.

[11] Patent Number: 5,873,864
[45] Date of Patent: Feb. 23, 1999

[54] CATHETER WITH BEVELED NEEDLE TIP

[75] Inventors: Ronald B. Luther, Newport Beach; Charles W. Dickerson, Tustin, both of Calif.; Roddy J.H. Clarke, Altharetta, Ga.

[73] Assignee: Luther Medical Products, Inc., Tustin, Calif.

[21] Appl. No.: 573,647

[22] Filed: Dec. 18, 1995

[51] Int. Cl.[6] .................................................. A61M 31/00
[52] U.S. Cl. ............................ 604/280; 604/93; 604/175
[58] Field of Search .................................. 604/264, 272, 604/93, 175, 164, 280, 283, 49, 51, 53, 52

[56] References Cited

U.S. PATENT DOCUMENTS

| | | |
|---|---|---|
| 2,847,995 | 8/1958 | Adams . |
| 3,358,684 | 12/1967 | Marshall ................................ 604/272 |
| 3,463,152 | 8/1969 | Sorenson . |
| 3,509,880 | 5/1970 | Guttman ................................ 604/272 |
| 3,536,073 | 10/1970 | Farb . |
| 3,584,624 | 6/1971 | de Ciutiis ........................... 604/272 X |
| 4,108,175 | 8/1978 | Orton . |
| 4,160,450 | 7/1979 | Doherty . |
| 4,500,312 | 2/1985 | McFarlane ............................. 604/263 |
| 4,588,398 | 5/1986 | Daugherty et al. ..................... 604/265 |
| 4,631,057 | 12/1986 | Mitchell .................................. 604/198 |
| 4,664,653 | 5/1987 | Sagstetter et al. ..................... 604/197 |
| 4,664,654 | 5/1987 | Strauss .................................... 604/198 |
| 4,676,783 | 6/1987 | Jagger et al. ............................ 604/171 |
| 4,684,369 | 8/1987 | Wildemeersch ........................ 604/272 |
| 4,702,738 | 10/1987 | Spencer .................................. 604/198 |
| 4,747,831 | 5/1988 | Kulli ....................................... 604/110 |
| 4,762,516 | 8/1988 | Luther et al. ........................... 604/164 |
| 4,778,453 | 10/1988 | Lopez ..................................... 604/110 |
| 4,781,692 | 11/1988 | Jagger et al. ............................ 604/164 |
| 4,826,490 | 5/1989 | Byrne et al. ............................. 604/198 |
| 4,828,549 | 5/1989 | Kvalo ..................................... 604/164 |
| 4,832,696 | 5/1989 | Luther et al. ........................... 604/164 |
| 4,834,718 | 5/1989 | McDonald .............................. 604/195 |
| 4,950,252 | 8/1990 | Luther et al. ........................... 604/198 |
| 5,135,502 | 8/1992 | Koenig et al. .......................... 604/164 |
| 5,364,374 | 11/1994 | Morrison et al. ....................... 604/272 |
| 5,403,283 | 4/1995 | Luther .................................... 604/164 |

FOREIGN PATENT DOCUMENTS

| | | |
|---|---|---|
| 139872 | 5/1985 | European Pat. Off. . |
| 023580 | 4/1980 | Germany . |

OTHER PUBLICATIONS

"The First Line of Defense Against Needle Stick Injuries", Introducing The ICU HR Needle, by ICU Medical, Inc., 3 pgs.

*Primary Examiner*—John D. Yasko
*Attorney, Agent, or Firm*—Stetina Brunda Garred & Brucker

[57] ABSTRACT

A catheter comprising a flexible proximal portion and a rigid distal portion having a beveled needle tip. The beveled tip overcomes coring of a barrier such as a septum of an implanted percutaneous drug delivery port when the needle tip passes therethrough for ultimate insertion of the catheter within the port. The invention also includes a catheter assembly incorporating the above-defined catheter along with a hand-operable implantation grip having a stylet member extending into the catheter and two opposing parallel finger members adjacent the catheter therebetween for holding the catheter during introduction thereof into an implanted percutaneous drug delivery port. The invention additionally includes methodology for catheterizing a percutaneous drug delivery port implanted in a living being through utilization of the catheter assembly and manually manipulating the grip thereof to insert the catheter tip into the port for long term implantation.

15 Claims, 2 Drawing Sheets

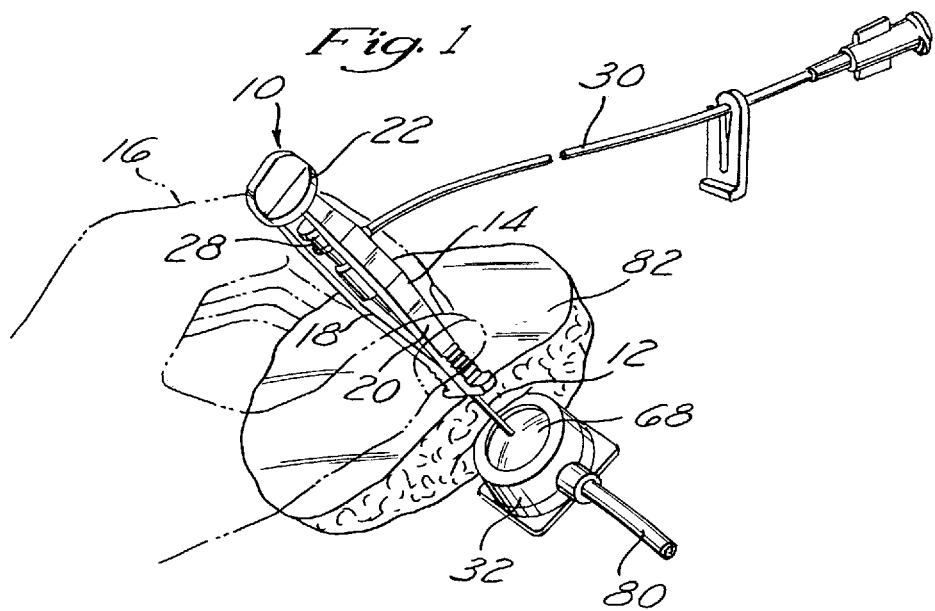
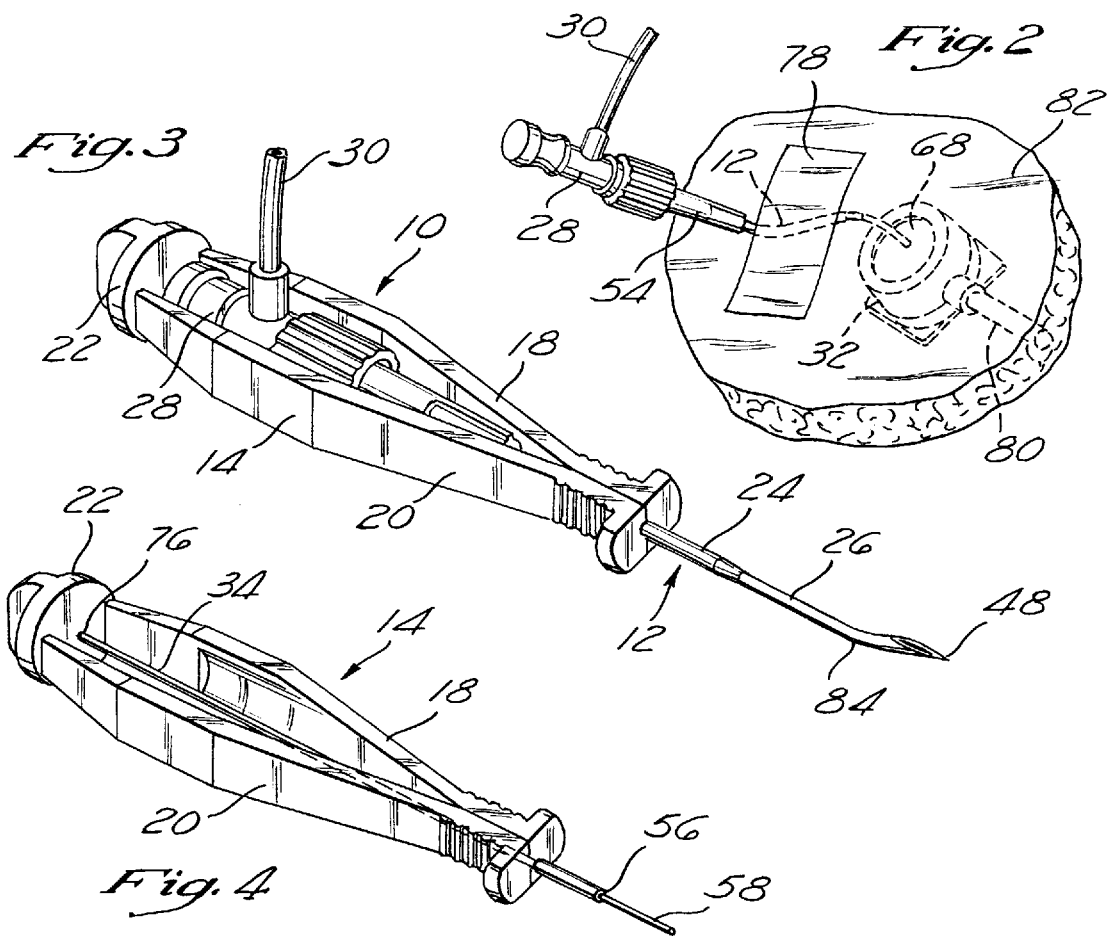

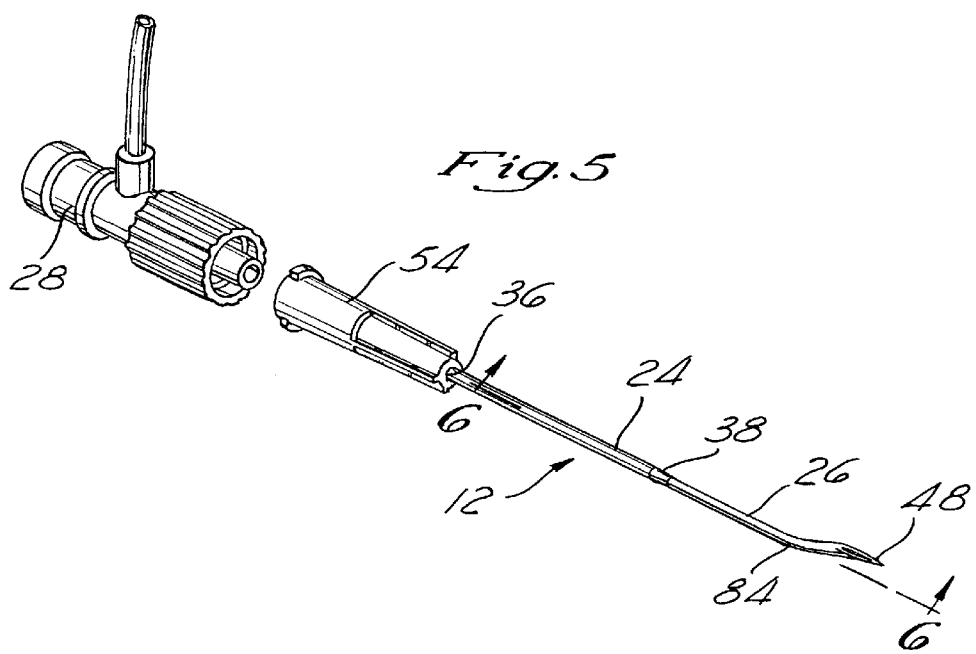
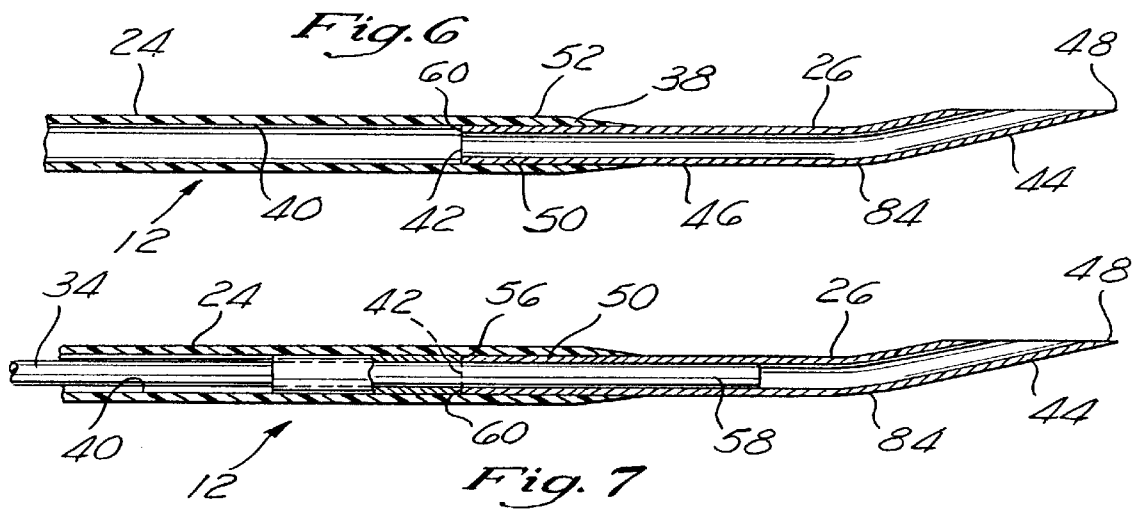
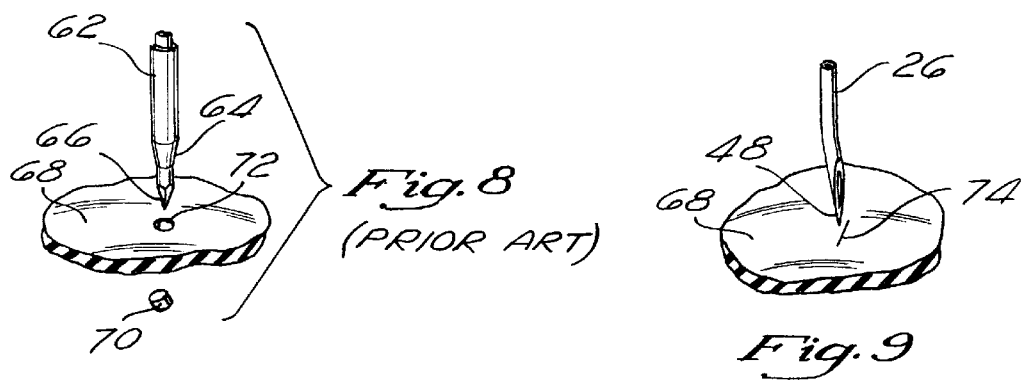

CATHETER WITH BEVELED NEEDLE TIP

BACKGROUND OF THE INVENTION

I. Field of the Invention

The present invention relates to a catheter having a flexible proximal portion and a rigid distal portion whose end has a beveled needle tip for direct insertion through a barrier without requiring an introducer tool to puncture a site of placement. The present invention includes a catheter assembly incorporating the catheter along with a hand-operable implantation grip, as well as methodology for introducing the catheter into a percutaneous drug delivery port implanted in a person.

II. Description of the Prior Art

Employment of a catheter for delivering a fluid medication to a patient is well known. Such a known catheter typically is a flexible tube whose distal end resides within the patient and whose proximal end has a hub fitting such as Luer-type fitting for connection to a reservoir from which medication is dispensed for travel through the catheter and into the patient. The distal end of the catheter may feed, for example, directly into a vein of the patient, or it may feed into a drug-delivery port implanted percutaneously within the patient. Such a port usually comprises a reservoir having a resilient septum disposed nearest the skin and through which the distal end of the catheter must pass to thereby deliver medication into the reservoir for subsequent outward flow to a medication site.

Because the entire prior-art catheter is constructed of a flexible material, the distal end thereof cannot be introduced into the patient without first employing another device to puncture the site of entry and provide an opening through which the distal end can pass. One approach for introducing the catheter is to use a hollow-needle syringe disposed within the catheter such that the needle produces an opening and simultaneously carries the surrounding catheter portion through the opening to the desired destination site. Thereafter, the syringe is withdrawn and the catheter remains. When this approach is used in entering a percutaneous drug delivery port, however, the syringe needle causes coring of the septum which, in turn, can cause the port to leak fluid through the produced hole. When this occurs, leaked medication originally intended to be delivered from the port to a specified body site is not available.

One approach for solving the coring problem when introducing a catheter into a percutaneous port has been employment of a solid stylet disposed within the catheter during catheter introduction and projecting from the distal end thereof such that the stylet punctures the septum and simultaneously carries the surrounding catheter portion through the puncture and into the reservoir of the port. The stylet, which is subsequently withdrawn, does not produce coring because it is of solid construction. Both U.S. Pat. Nos. 5,135,502 and 5,403,283 teach solid stylets, with the latter patent additionally teaching an insertion tool whose construction can include stylet isolation means activated after catheter insertion to thereby guard against an inadvertent needle stick to a health care provider.

While using a solid stylet as described above alleviates the coring problem while entering a percutaneous port, for example, the catheter still can be introduced only by using a separate piercing tool. This necessity requires the use of, as well as the disposal of, the stylet piercing tool which, because it has entered a patient site, can be a health hazard after withdrawal from the patient and prior to final disposal.

It is therefore apparent that a need is present for a catheter whose construction permits ready introduction within a patient site. Accordingly, a primary object of the present invention is to provide a catheter comprising a flexible proximal portion and a rigid distal portion, with the distal portion having a needle tip for directly piercing a barrier and entering a site for medication delivery.

Another object of the present invention is to provide a catheter wherein the needle tip of the distal portion is beveled to thereby eliminate coring by the needle tip.

Yet another object of the present invention is to provide a catheter assembly incorporating a catheter having a beveled needle tip and a hand-operable implantation grip whereby catheter placement and insertion is aided.

Still another object of the present invention is to provide a method of catheterizing an implanted percutaneous drug delivery port through the utilization of a catheter assembly to achieve implantation of a catheter having a needle tip beveled to thereby enter a septum of the port without coring the septum during entry.

These and other objects of the present invention will become apparent throughout the description of the invention which now follows.

SUMMARY OF THE INVENTION

The present invention is a catheter comprising a flexible proximal portion and a rigid distal portion having a beveled needle tip. The proximal and distal portions are in axial alignment with each other and secured to each other at a junction site. In a preferred embodiment the proximal portion is a plastic, the distal portion is a metal, and the needle tip is beveled at an angle of from about 10 degrees to about 80 degrees. The beveled tip overcomes coring of a barrier such as a septum of an implanted percutaneous drug delivery port when the needle tip passes therethrough for ultimate implantation of the catheter within the port.

The present invention also includes a catheter assembly incorporating the above-defined catheter along with a hand-operable implantation grip for holding the catheter during introduction of the second end of the distal portion thereof into an implanted percutaneous drug delivery port. The grip comprises a frame having a top member with two opposing parallel finger members adjacent the catheter therebetween and extending from the top member a distance sufficient to be adjacent at least a part of the proximal portion of the catheter. The finger members are biased toward each other and are of sufficient flexibility to be movable away from each other. A stylet member extends from the top member between the opposing finger members and is inserted in axial alignment within the catheter. The stylet member is of sufficient length to extend to a site within the distal portion of the catheter to thereby function as a support within the catheter during its introduction into the drug delivery port. The present invention includes a method of catheterizing a percutaneous drug delivery port implanted in a living being through utilization of the catheter assembly. Manual manipulation of and pressure to the implantation grip provides stability to the catheter while its needle tip is forced through a septum of the drug delivery port. Thereafter, the grip is manually removed from the catheter and the catheter tip remains within the drug delivery port for subsequent introduction of medication to the port.

BRIEF DESCRIPTION OF THE DRAWINGS

An illustrative and presently preferred embodiment of the invention is shown in the accompanying drawings in which:

FIG. 1 is a perspective view of a catheter assembly wherein the catheter thereof is being inserted into a percutaneous drug delivery port implanted in a living being;

FIG. 2 is a perspective view of the catheter of FIG. 1 in place after removal of a hand operable grip of the catheter assembly;

FIG. 3 is a perspective view of the catheter assembly showing the catheter in place;

FIG. 4 is a perspective view of the hand operable grip of the catheter assembly without the presence of the catheter;

FIG. 5 is a perspective view the catheter disassembled from a T-connector to which a second catheter can be attached as shown in FIG. 1;

FIG. 6 is a partial cross section view of the catheter of FIG. 5 along line 6—6 thereof;

FIG. 7 is a partial cross section view of the catheter of FIG. 5, except with the stylet of the hand operable grip there within;

FIG. 8 is a prior art perspective view of a non-beveled needle tip upon insertion through a sectional portion of a septum of a drug delivery port; and FIG. 9 is a perspective view of the beveled needle tip of the catheter of FIG. 5 upon insertion through a sectional portion of a septum of a drug delivery port.

DETAILED DESCRIPTION OF THE PREFERRED EMBODIMENT

Referring to FIGS. 1 through 4, a catheter assembly 10 comprising a catheter 12 and a hand-operable implantation grip 14 is shown. The assembly 10 is illustrated in operation in FIG. 1 as fingers of a hand 16 (shown in phantom lines) act to squeeze opposing parallel finger members 18, 20 adjacent the catheter 12 therebetween and extending from a top member 22 of the grip 14. The catheter 12 has a proximal portion 24 and a distal portion 26 as shown in FIGS. 2 and 3 and more clearly illustrated in FIG. 5 which will be discussed below. Finger members 18, 20 extend a distance sufficient to be adjacent at least a part of the proximal portion 24 of the catheter 12, and are biased toward each other to contact the proximal portion 24 while being sufficiently flexible to be hand movable away from each other for removal of the grip 14 from the catheter 12. Connected to the top of the proximal portion 24 of the catheter 12 is a standard T-connector 28 (shown more clearly in FIG. 5) likewise situated between the finger members 18, 20. A second catheter 30 as shown in FIG. 1 can be attached to the T-connector 28 for delivery of a fluid to be ultimately directed through the catheter 12 to an implanted percutaneous drug delivery port 32 as shown in FIGS. 1 and 2. The grip 14 has a stylet member 34 extending from the top member 22 to be inserted in axial alignment within the catheter 12 and of sufficient length to extend to a site within the distal portion 26 of the catheter 12. In the embodiment here shown, the stylet member 34 is made of metal and the remaining components of the grip 14 are made of plastic. The proximal end 76 of the stylet member 34 is embedded within the top member 22 of the grip 14.

Construction of the catheter 12 of the present invention is shown in FIGS. 5 and 6. Specifically, the catheter 12 has a flexible proximal portion 24, preferably made of a plastic, and a rigid distal portion 26, preferably made of a metal such as stainless steel, in axial alignment with each other. The proximal portion 24 has a first end 36, a second end 38, and an inside wall 40. The distal portion 26 has a first end 42, a second end 44, and an outside wall 46, and can have an angle 84 therein if desired in accord with configuration preference. The second end 44 of the distal portion 26 is a needle tip 48 beveled preferably at an angle of from about 10 degrees to about 80 degrees. The proximal portion 24 and distal portion 26 are secured to each other at a junction where a section 50 of the first end 42 of the distal portion 26 is disposed within a section 52 of the second end 38 of the proximal portion 24 to thereby position a section of the inside wall 40 of the proximal portion 24 adjacent a section of the outside wall 46 of the distal portion 26. An adhesive is disposed between these adjacent wall sections to thereby maintain a secured union. A hub fitting 54 such as a Luer fitting is disposed at the first end 36 of the proximal portion 24 for cooperative attachment of the catheter 12 to a fluid delivery apparatus such as a T-connector 28 to which another catheter 30 (as discussed above in relation to FIG. 1) can be attached.

FIG. 7 shows a cross section of the catheter 12 as it would appear as part of the catheter assembly 10 illustrated in FIGS. 1 and 3. In particular, the stylet member 34 of the grip 14 is disposed within the catheter 12 and extends into the distal portion 26 thereof. As shown in FIGS. 4 and 6, the stylet member 34 has a shoulder 56 near its distal end 58. This shoulder 56 abuts the lip 60 of the first end 42 of the distal portion 26 of the catheter 12 when the catheter assembly 10 is intact.

As earlier described, a prior art approach to introducing a catheter into an implanted drug delivery port employs a hollow-needle syringe disposed within the catheter such that the needle produces an opening in the septum of the port and simultaneously carries the surrounding catheter portion through the opening to the interior of the port. However, because the hollow needle of the syringe has non-beveled tip, coring occurs as shown in the prior-art illustration of FIG. 8. Specifically, a prior-art flexible catheter 62 has extending from its distal end 64 a syringe needle 66. When the needle 66 is forced through a section of a septum 68 of a drug delivery port to thereby introduce the catheter therein, coring of the septum 68 occurs and a removed fragment 70 of the septum 68 enters the port. Additionally, a hole 72 results in the septum 68, thereby allowing fluid within the port to improperly leak out. This condition is contrasted with that illustrated in FIG. 9 where a catheter of the present invention is used to enter through the septum 68. As shown, when the beveled needle tip 48 of the distal portion 26 enters the septum, it leaves only a slit 74 which effectively seals to prevent leakage.

In operation, the catheter assembly 10 is used in the following manner to accomplish catheter introduction into a percutaneous port. An operator manually urges the finger members 18, 20 of the grip 14 toward each other to thereby apply lateral pressure to the catheter 12 therebetween and maintain physical stability thereof. The operator then places the needle tip 48 at an appropriate cutaneous entry site for the implanted port 32 (shown in FIGS. 1 and 2) which generally is the septum 68 as located nearest the skin, and thereafter applies sufficient pressure to introduce the needle tip 48 percutaneously through the septum 68 and into the port 32. After such placement, the operator urges the finger members 18, 20 away from each other and withdraws the grip 14 from the catheter 12. As is apparent from the illustration of FIG. 4, the stylet member 34 extends through the catheter 12 (as well as through the T-connector 28) and therefore must be withdrawn from the catheter and T-connector in a generally axial manner. The needle tip 48 remains within the port 32 and is the entry lumen for fluid communication with the catheter 12. As shown in FIG. 2, a tape 78 can be used to maintain the catheter 12 in place on the skin 82 of the patient. Fluid medication is then introduced into the catheter 12 for delivery to the port 32 from which the medication flows to a designated site within the body through an outlet tube 80. The present invention therefore not only provides a catheter insertable without a separate puncture tool, but also provides a catheter requiring no disposal of any component thereof that has been exposed to bodily fluids of a patient until the entire catheter is removed at a later date.

While an illustrative and presently preferred embodiment of the invention has been described in detail herein, it is to be understood that the inventive concepts may be otherwise variously embodied and employed and that the appended claims are intended to be construed to include such variations except insofar as limited by the prior art.

We claim:

1. A catheter assembly for accessing a percutaneous drug delivery port implanted in a living being, the assembly comprising:
    a) a catheter comprising a flexible proximal portion having a first end, a second end and an inside wall, and a rigid distal portion having a first end with a lip, a second end and an outside wall, with the proximal and distal portions in axial alignment with each other and secured to each other at a junction of a section of the second end of the proximal portion and a section of the first end of the distal portion, and further with the second end of the distal portion having a beveled needle tip; and
    b) a hand-operable implantation grip for holding the catheter during introduction of the second end of the distal portion thereof into the port, the grip comprising:
        i.) a frame having a top member with two opposing parallel finger members adjacent the catheter therebetween and extending from the top member a distance sufficient to be adjacent at least a part of the proximal portion of the catheter, with the finger members biased toward each other and of sufficient flexibility to be movable away from each other; and
        ii.) a stylet member extending from the top member between the opposing finger members and inserted in axial alignment within the catheter, with the stylet member having a distal end and being of sufficient length to extend to a site within the distal portion of the catheter.

2. A catheter assembly as claimed in claim 1 wherein the flexible proximal portion of the catheter is a plastic, the rigid distal portion of the catheter is a metal, and the needle tip is beveled at an angle of from about 10 degrees to about 80 degrees.

3. A catheter assembly as claimed in claim 2 wherein the section of the first end of the distal portion of the catheter is disposed within the section of the second end of the proximal portion thereof to thereby position a section of the inside wall of the proximal portion adjacent a section of the outside wall of the distal portion.

4. A catheter assembly as claimed in claim 3 wherein a shoulder is disposed near the distal end of the stylet to thereby abut the lip of the first end of the distal portion of the catheter.

5. A catheter assembly as claimed in claim 4 wherein an adhesive is disposed between the sections of the inside wall and outside wall of the catheter adjacent each other.

6. A catheter assembly as claimed in claim 5 wherein a hub fitting is disposed at the first end of the proximal portion of the catheter.

7. A method of catheterizing a percutaneous drug delivery port implanted in a living being, the method comprising:
    a) providing a catheter assembly comprising:
        i.) a catheter comprising a flexible proximal portion having a first end, a second end and an inside wall, and a rigid distal portion having a first end with a lip, a second end and an outside wall, with the proximal and distal portions in axial alignment with each other and secured to each other at a junction of a section of the second end of the proximal portion and a section of the first end of the distal portion, and further with the second end of the distal portion having a beveled needle tip; and
        ii.) a hand-operable implantation grip for holding the catheter during introduction of the second end of distal portion thereof into the port, the grip comprising:
            1) a frame having a top member with two opposing parallel finger members adjacent the catheter therebetween and extending from the top member a distance sufficient to be adjacent at least a part of the proximal portion of the catheter, with the finger members biased toward each other and of sufficient flexibility to be movable away from each other; and
            2) a stylet member extending from the top member between the opposing finger members and inserted in axial alignment within the catheter, the stylet member having a distal end and being of sufficient length to extend to a site within the distal portion of the catheter;
    b) manually urging the finger members of the implantation grip toward each other to thereby apply lateral pressure to the catheter therebetween and maintain physical stability thereof;
    c) placing the needle tip of the distal portion of the catheter at an appropriate cutaneous entry site for the port and applying sufficient pressure to introduce the needle tip percutaneously into the port; and
    d) manually urging the finger members of the implantation device away from each other and withdrawing the stylet from the catheter and thereby releasing the catheter for subsequent use in the introduction of fluid into the port.

8. The method of claim 7 wherein the flexible proximal portion of the catheter is a plastic, the rigid distal portion of the catheter is a metal, and the needle tip of the catheter is beveled at an angle of from about 10 degrees to about 80 degrees.

9. The method of claim 8 wherein the section of the first end of the distal portion of the catheter is disposed within the section of the second end of the proximal portion thereof to thereby position a section of the inside wall of the proximal portion adjacent a section of the outside wall of the distal portion.

10. The method of claim 9 wherein a shoulder is disposed near the distal end of the stylet to thereby abut the lip of the first end of the distal portion of the catheter.

11. The method of claim 10 wherein an adhesive is disposed between the sections of the inside wall and outside wall of the catheter adjacent each other.

12. The method of claim 11 wherein a hub fitting is disposed at the first end of the proximal portion of the catheter.

13. A catheter comprising a flexible proximal portion having a first end with a hub fitting, a second end and an inside wall, and a rigid distal portion having a first end, a second end and an outside wall, with the proximal and distal portions in axial alignment with each other and secured to each other at a junction of a section of the second end of the proximal portion and a section of the first end of the distal portion whereby the section of the first end of the distal portion is disposed within the section of the second end of the proximal portion to thereby position a section of the inside wall of the proximal portion adjacent a section of the outside wall of the distal portion and wherein an adhesive is disposed between the sections of the inside wall and outside wall adjacent each other, and further wherein the proximal portion is a plastic, the distal portion is a metal, and the second end of the distal portion has a needle tip beveled at an angle of from about 10 degrees to about 80 degrees.

14. A catheter assembly for accessing a percutaneous drug delivery port implanted in a living being, the assembly comprising:
   a) a catheter comprising a flexible proximal portion having a first end with a hub fitting, a second end and an inside wall, and a rigid distal portion having a first end with a lip, a second end and an outside wall, with the proximal and distal portions in axial alignment with each other and secured to each other at a junction of a section of the second end of the proximal portion and a section of the first end of the distal portion whereby the section of the first end of the distal portion is disposed within the section of the second end of the proximal portion to thereby position a section of the inside wall of the proximal portion adjacent a section of the outside wall of the distal portion and wherein an adhesive is disposed between the sections of the inside wall and outside wall adjacent each other, and further wherein the proximal portion is a plastic, the distal portion is a metal, and the second end of the distal portion has a needle tip beveled at an angle of from about 10 degrees to about 80 degrees as measured from a horizontal plane; and
   b) a hand-operable implantation grip for holding the catheter during introduction of the second end of distal portion thereof into the port, the grip comprising:
      i.) a frame having a top member with two opposing parallel finger members adjacent the catheter therebetween and extending from the top member a distance sufficient to be adjacent at least a part of the proximal portion of the catheter, with the finger members biased toward each other and of sufficient flexibility to be movable away from each other; and
      ii.) a stylet member extending from the top member between the opposing finger members and inserted in axial alignment within the catheter, the stylet member having a distal end and being of sufficient length to extend to a site within the distal portion of the catheter, with the stylet having a shoulder disposed near the distal end thereof to thereby abut the lip of the first end of the distal portion of the catheter.

15. A method of catheterizing a percutaneous drug delivery port implanted in a living being, the method comprising:
   a) providing a catheter assembly comprising:
      i.) a catheter comprising a flexible proximal portion having a first end with a hub fitting, a second end and an inside wall, and a rigid distal portion having a first end with a lip, a second end and an outside wall, with the proximal and distal portions in axial alignment with each other and secured to each other at a junction of a section of the second end of the proximal portion and a section of the first end of the distal portion whereby the section of the first end of the distal portion is disposed within the section of the second end of the proximal portion to thereby position a section of the inside wall of the proximal portion adjacent a section of the outside wall of the distal portion and wherein an adhesive is disposed between the sections of the inside wall and outside wall adjacent each other, and further wherein the proximal portion is a plastic, the distal portion is a metal, and the second end of the distal portion has a needle tip beveled at an angle of from about 10 degrees to about 80 degrees; and
      ii.) a hand-operable implantation grip for holding the catheter during introduction of the second end of distal portion thereof into the port, the grip comprising:
         1) a frame having a top member with two opposing parallel finger members adjacent the catheter therebetween and extending from the top member a distance sufficient to be adjacent at least a part of the proximal portion of the catheter, with the finger members biased toward each other and of sufficient flexibility to be movable away from each other; and
         2) a stylet member extending from the top member between the opposing finger members and inserted in axial alignment within the catheter, the stylet member having a distal end and being of sufficient length to extend to a site within the distal portion of the catheter, the stylet having a shoulder disposed near the distal end thereof to thereby abut the lip of the first end of the distal portion of the catheter;
   b) manually urging the finger members of the implantation grip toward each other to thereby apply lateral pressure to the catheter therebetween and maintain physical stability thereof;
   c) placing the needle tip of the distal portion of the catheter at an appropriate cutaneous entry site for the port and applying sufficient pressure to introduce the needle tip percutaneously into the port; and
   d) manually urging the finger members of the implantation device away from each other and withdrawing the stylet from the catheter and thereby releasing the catheter for subsequent use in the introduction of fluid into the port.

* * * * *